| United States Patent [19] | [11] Patent Number: 4,668,638 |
| Janoff et al. | [45] Date of Patent: *May 26, 1987 |

[54] LIPOSOME COMPOSITION FOR LUPUS ASSAY

[75] Inventors: Andrew S. Janoff, Lawrenceville; Marc J. Ostro, North Brunswick; Alan L. Weiner, Plainsboro, all of N.J.; Gerald Weissmann, New York, N.Y.; James R. Seibold, Piscataway, N.J.

[73] Assignee: The Liposome Company, Inc., Princeton, N.J.

[*] Notice: The portion of the term of this patent subsequent to Jan. 14, 2003 has been disclaimed.

[21] Appl. No.: 535,884

[22] Filed: Sep. 26, 1983

Related U.S. Application Data

[63] Continuation-in-part of Ser. No. 476,495, Mar. 24, 1983, Pat. No. 4,564,599, and a continuation-in-part of Ser. No. 410,249, Aug. 23, 1982, abandoned, and a continuation-in-part of Ser. No. 362,382, Mar. 26, 1982, abandoned.

[51] Int. Cl.$^4$ ............... G01N 33/564; B32B 5/16; B32B 9/02; B32B 9/04
[52] U.S. Cl. ................... 436/506; 264/4.6; 436/507; 436/829; 428/402.2
[58] Field of Search ............ 436/506, 507, 829; 428/402.2; 264/4.6

[56] References Cited

U.S. PATENT DOCUMENTS

| 4,235,792 | 11/1980 | Hsia et al. | 436/829 |
| 4,329,331 | 5/1982 | Kallick | 436/506 |
| 4,448,765 | 5/1984 | Ash et al. | 436/829 |

FOREIGN PATENT DOCUMENTS

WO80/00026  1/1980  PCT Int'L Appl. ............ 436/506

OTHER PUBLICATIONS

Schieren, H. et al., Biochem. and Biophys. Res. Comm., 82 (4), pp. 1160–1167 (1978).
Weissmann, G. et al., I: J. Clin. Inves. 53, pp. 536–543 (Feb. 1974).
Weissmann, G. et al., II: Proc. Natl. Acad. Sci. U.S.A. 73(2), pp. 510–514 (Feb. 1976).

*Primary Examiner*—Sidney Marantz
*Assistant Examiner*—L. Krawczewicz
*Attorney, Agent, or Firm*—Pennie & Edmonds

[57] ABSTRACT

An immunoassay utilizing a novel liposome composition in which there is incorporated a stabilizing or destabilizing component and an antigen. The presence of cognate antibodies in test samples is detected by the alteration of the supramolecular structure of the liposomes resulting in changes in stabilization. Destabilization can be detected, and in certain cases, caused by, the addition of magnesium or calcium ions. Increased stabilization can be detected by the polymerization of bilayer components in response to ultraviolet light. Antibody-antigen interactions at the liposome surface mediate the stabilization/destabilization response.

57 Claims, No Drawings

LIPOSOME COMPOSITION FOR LUPUS ASSAY

The present application is a continuation-in-part application of application Ser. No. 476,495 filed Mar. 24, 1983, which issued as U.S. Pat. No. 4,564,599 and a continuation-in-part of Ser. No. 410,249, filed Aug. 23, 1982, now abandoned and a continuation-in-part application of application Ser. No. 362,382, filed Mar. 26, 1982, now abandoned all of which are incorporated herein by reference.

TABLE OF CONTENTS

1. Field of the Invention
2. Background of the Invention
   2.1. Immunoassays
   2.2. Autoimmune Diseases
      2.2.1. Systemic Lupus Erythematosis
   2.3. Diagnosis of Autoimmune Disease
      2.3.1. Diagnostic Assays for SLE
   2.4. Liposomes
3. Summary of the Invention
4. Description of the Invention
   4.1. Liposomes
      4.1.1. The Antigens
      4.1.2. Liposomes Incorporating a Destabilizing Component
      4.1.3. Liposomes Incorporating a Stabilizing Component
   4.2. Diagnostic Assays
      4.2.1. Embodiment I
      4.2.2. Embodiment II
      4.2.3. Embodiment III
5. Example: Immunoassays for SLE
   5.1. Example 1: Preparation of Liposomes
   5.2. Example 2: Preparation of Anionic Lipids for Embodiment II
   5.3. Example 3: Embodiment I
   5.4. Example 4: Embodiment II
   5.5. Example 5: Embodiment III
   5.6. Example 6: Blind Studies

1. FIELD OF THE INVENTION

The present invention pertains to immunoassays utilizing novel liposome compositions. The immunoassays described herein may be used for the detection of antibodies present in test solutions (such as sera) or as competition immunoassays for the detection of antigens in test solutions. The immunoassays described herein are particularly useful as diagnostic assays for autoimmune diseases. The method of the invention is demonstrated herein by way of example for selectively detecting the presence of antibodies which are produced by patients suffering from systemic lupus erythematosis.

2. BACKGROUND OF THE INVENTION

2.1 IMMUNOASSAYS

The identification and quantification of various biological materials using immunoassays offers advantages over common chemical tests, spectroscopic methods, and methods which determine physical parameters (e.g., sedimentation coefficients, electrophoretic mobilities, chromatographic constants, etc.), in that the material can be detected with greater specificity. Immunoassays currently used include radio immunoassays, fluorescent immunoassays, and enzymatic immunoassays. Some disadvantages of the various immunoassay methods currently used include the following: (1) radiolabels used in radio immunoassays have a limited stability and require special handling as well as special means for disposal; (2) fluorescent immunoassays often require separation steps in the procedure, and the fluorescent label may be quenched by a variety of agents present in test solutions; (3) enzyme immunoassays are tedious and can be more difficult to quantitate.

Some recent reports describe the use of liposomes in immunoassays. The liposome membranes are labeled with specific antigens or antibodies and entrap an enzyme or substrate; these liposomes are ruptured in the presence of cognate antibody and serum complement. Release of the liposome-entrapped enzyme can be detected by the addition of the appropriate enzyme substrate to the test solution. However, because the diffusion of macromolecules (such as enzymes) through lesions produced by complement in the liposome bilayer is much slower than the diffusion rate of small molecules the speed and sensitivity of these assays is hampered.

2.2. AUTOIMMUNE DISEASES

The main functions of the immune system are to provide resistance to foreign cells and substances and to destroy malignant cells. This requires an effective mechanism which distinguishes self from nonself. Autoimmunity involves an error in this system that gives rise to an immunological attack on the body's own cells and tissue.

Autoimmunity is a primary cause or secondary contribution to a number of diseases. For example, blood sera of patients with a relatively rare disease, paroxysmal cold hemoglobinuria, contain autoantibodies that combine with the patient's own red blood cells. Several of the commoner forms of human anemia, have been shown to be associated with autoantibodies directed against red blood cells.

A number of antireceptor autoimmune disorders have been described. For example, antibodies against islet cells of the pancreas have been detected in severe forms of diabetes mellitus. Antibodies reactive with acetylcholine receptors are detected in the sera of patients suffering from myasthenia gravis; these antibodies affect the transmission of signals across neuromuscular junctions, resulting in muscular weakness and in severe cases, respiratory arrest. In patients with Graves' disease, antibodies that react with human thyroid cells are detected; these antibodies stimulate the thyroid cells to over produce thyroid hormones causing restlessness, weight loss and palpitations.

The epitome of autoimmune disorders in humans is systemic lupus erythrematosis (SLE) (described in detail in Section 2.2.1). In this disease, the patient manufactures a myriad of autoantibodies directed against different constituents of the body.

Table I (from, The Merck Manual, Volume 1, General Medicine, 14th Edition, 1982, Robert Berkow, M.D. (ed.)) lists a number of known autoimmune disorders.

TABLE I

| AUTOIMMUNE DISORDERS | |
|---|---|
| Disorder | Mechanism or Evidence |
| Hashimoto's thyroidites | Cell-mediated and humoral thyroid cytotoxicity |
| Systemic lupus erythematosus | Circulating immune complexes |
| Goodpasture's syndrome | Anti-basement membrane antibody |

TABLE I-continued

| | |
|---|---|
| Pemphigus | Epidermal acantholytic antibody |
| Receptor autoimmunity Graves' disease | TSH receptor antibody (stimulatory) |
| Myasthenia gravis | Acetylcholine receptor antibody |
| Insulin resistance | Insulin receptor antibody |
| Autoimmune hemolytic anemia | Phagocytosis of antibody-sensitized erythrocytes |
| Autoimmune thrombocytopenic purpura | Phagocytosis of antibody-sensitized platelets |
| Probable Autoimmune Disorders: | |
| Rheumatoid arthritis | Immune complexes in joint |
| Progressive systemic sclerosis | Nucleolar and other nuclear antibody |
| Mixed connective tissue disease | Antibody to extractable nuclear antigen (ribonucleoprotein) |
| Pernicious anemia | Anti-parietal cell and intrinsic factor antibodies |
| Idiopathic Addison's disease | Humoral and (?) cell-mediated adrenal cytotoxicity |
| Infertility (some cases) | Antispermatozoal antibodies |
| Glomerulonephritis | Glomerular basement membrane antibody, or immune complexes |
| Bullous pemphigoid | IgG and complement in basement membrane |
| Sjogren's syndrome | Multiple tissue antibodies |
| Diabetes mellitus (some) | Cell-mediated and humoral islet cell antibodies |
| Adrenergic drug resistance (some asthmatics) | $\beta$-adrenergic receptor antibody |
| Possible Autoimmune Disorders: | |
| Chronic active hepatitis | Smooth muscle antibody |
| Primary biliary cirrhosis | Mitochondrial antibody |
| Other endocrine gland failure | Specific tissue antibody in some cases |
| Vitiligo | Melanocyte antibody |
| Vasculitis | Some cases: Immunoglobulin and complement in vessel walls, low serum complement |
| Post-myocardial infarction, cardiotomy syndrome | Myocardial antibody |
| Many other inflammatory, granulomatous, degenerative, and atrophic disorders | No reasonable alternative explanation |

2.2.1. SYSTEMIC LUPUS ERYTHEMATOSIS

SLE is a serious autoimmune condition in which abnormal humoral and cellular immune responses occur. Patients with this immune complex disorder manifest symptoms such as erosive inflammation of skin (producing a characteristic rash), blood vessel lesions, pleuresy, psychiatric disturbances, convulsions, and inflammation of the kidney glomeruli (leading to renal disfunction or failure). Although various factors have been attributed to the onset of SLE, the precise etiology is not known. It is known that significant concentrations of both gamma-globulins and complement are present in the tissues and such immune complexes are considered the causative agents for the systemic cellular damage which is observed. A wide range of auto-antibodies have been detected in SLE patients including circulating antibodies to lymphocytes, red blood cells, platelets and neutrophils and recognition occurs by all four subclasses of immunoglobulin to cellular components such as nuclei, ribosomes, mitochondria and lysosomes.

The sites of lupus antibody interaction with subcellular components include nucleoproteins, histones and nucleic acids. In the case of nucleic acids, one antigenic determinent appears to be the carbohydrate-phosphate unit.

2.3. DIAGNOSIS OF AUTOIMMUNE DISEASE

If autoimmunity is suspected, based upon the clinical symptoms manifested by the patient, then diagnosis involves detection of the relevant antibodies (Ig molecules) in the patient's serum. This may involve purifying the relevant antigen and mixing the antigen with the patient's serum. If antoantibodies are present in the patient's serum the antibodies will immunoreact with the purified antigen in vitro. After removal of unreacted Ig molecules (i.e., antibodies directed against foreign materials which are normally present in patients' sera), the bound autoantibodies can be detected by adding labeled anti-Ig (e.g., radiolabeled, fluorescent labeled, or enzyme labeled antibodies directed against human Ig). The immunoassays used to detect SLE are described below.

2.3.1. DIAGNOSTIC ASSAYS FOR SLE

One of the first diagnostic tests for SLE involved the observation that microscopic examination of an SLE blood sample which is allowed to stand at room temperature for several hours reveals unusual structural entities which apparently result from leukocytic phagocytosis of extruded nuclei from damaged lymphocytes through which antinuclear antibodies had passed. Such polymorphonuclear leukocytes which possess multiple nuclei containing DNA-antiDNA complexes or such nuclei surrounded by multiple leukocytes, termed "LE cells", appear in 75% of patients with SLE. They also may appear however in patients which rheumatoid arthritis, Sjorgren's Syndrome, scleroderma and hepatitis B. The presence of LE cells as an SLE assay thus is non-specific, which coupled with a lack of specificity for immune complexes, makes results ambiguous and their interpretation subjective.

A further SLE screening test involves the agglutination reaction between circulating antibodies and polystyrene particles modified on their surface with dinitrophenyl groups. The interaction of these groups with Fab sites on immunoglobulins produces agglutination and precipitation of the particles. This test is essentially qualitative and lacks specificity for SLE antibodies alone, the modified particles interacting with any other circulating immunoglobulin so as to produce false positive results.

At present the most commonly used tests for SLE are immunofluorescent assays for the presence of cellular antinuclear antibodies. Human epithelial cells in vitro are exposed to serum of SLE patients and antibodies to cellular components which bind to these cells then are recognized by incubation with fluorescein isothiocyanate linked anti-Ig. Various patterns of fluorescence can be correlated to antibodies for specific cell constituents; e.g., peripheral=anti-DNA, diffuse=anti-nucleoprotein, speckled=antiribonucleoprotein, nucleolar-=anti-RNA. This test is highly subjective and, as with the other tests discussed above, is not specific for SLE. Positive findings can be produced in patients with rheumatoid arthritis, schleroderma, Sjogren's Syndrome, liver disease, and pulmonary disease, as well as in patients receiving procainamide or hydralazine.

In another fluorescent assay, Clathridia protozoan are exposed to serum and the degree of binding to double stranded DNA in the mitochonchia is then recognized by incubation with fluorescein linked antibodies. This assay, while an improvement over the earlier methods, requires the use of a fluorescence microscope and detects only approximately 60% of those patients with lupus.

2.4. LIPOSOMES

Liposomes are completely closed bilayer membranes containing an entrapped aqueous phase. Liposomes may be any variety of unilamellar vesicles (possessing a single membrane bilayer) or multilamellar vesicles (onion-like structures characterized by concentric membrane bilayers each separated from the next by a layer of water).

The original liposome preparations of Bangham et al. (1965, J. Mol. Biol. 13:238–252) involved suspending phospholipids in an organic solvent which was then evaporated to dryness leaving a waxy deposit of phospholipid on the reaction vessel. Then an appropriate amount of aqueous phase was added, the mixture was allowed to "swell", and the resulting liposomes which consisted of multilamellar vesicles (MLVs) were dispersed by mechanical means. The resulting structure of the membrane bilayer is such that the hydrophobic (non-polar) "tails" of the lipid orient inward while the hydrophilic (polar) "heads" orient outward towards the aqueous phase.

Lipid vesicles can also be prepared by injection of the lipids in an organic phase into an aqueous solution as described by Batzri and Korn (Biochim. Biophys. Acta, 298:1015 [1973]) using ethanol and by Deamer and Bangham (Biochim. Biophys. Acta, 443:629–634 [1976]) using ether.

Liposomes bearing substances such as antigenic lipids, i.e., N-dinitrophenyl-aminocaproyl phosphatidylethanolamine (Lesserman et al., 1979, J. Immonol. 122:585–591), heat-aggregated IgM molecules (Weissman et al., 1975, Proc. Natl. Acad. Sci. U.S.A. 72:88–92), and sialoglycoprotein which binds lectins (Juliano and Stamp, 1976, Nature (London) 261:235–238)) have been used in vitro to enhance specific binding to cell surfaces. Huang et al., 1980, J. Biol. Chem. 255:8015–8018, incorporated anti-H-2-monoclonal antibody linked to palmitic acid into the lipid bilayer of liposomes. More recently, Martin and Papahadjopoulos have demonstrated targeting of liposome preparations by the covalent linkage of Fab' fragments via disulfide bonds to a derivate of phosphatidylethanolamine incorporated into the lipid bilayer (1982, J. Biol. Chem. 257:286–288; Martin, Hubbell and Papahadjopoulos, 1981, Biochem. 20:4229–4238).

3. SUMMARY OF THE INVENTION

The present invention involves immunoassays using liposomes containing a stablilizing component or a destabilizing component and an antigen incorporated into the liposomal membrane. The assays are based on the selective inhibition of either the stabilization or destabilization of the liposome membrane. This is mediated by the interaction of cognate antibodies present in the surrounding medium with the stabilizing or destabilizing component of the liposome membrane or with the antigen (cognate antibodies are defined as antibodies which are directed against the antigens incorporated into the liposome membrane).

Stabilization as used in the present invention refers to the preservation of the supramolecular structure or membrane architecture of the liposome. The precise mechanism by which this stabilization occurs is not fully understood. Destabilization is indicated by an increased permeability of the liposome resulting in a release of entrapped material into the external environment or a leak of external ions into the liposome aqueous space (influx). According to one mode of the present invention liposomes incorporating a destabilizing component are made to entrap an ion dependent indicator dye. Destabilization of the liposome membrane results in release of the entrapped dye or the influx of ions from the external environment into the aqueous space of the liposome. The assay medium is prepared so that the dye will change color once in contact with the medium; therefore, destabilization can be detected visually or spectrophotometrically by a color change in the indicator dye.

According to another mode of the present invention, the liposome membrane can be further stabilized by the addition of a stabilizing component. Stabilization is accomplished by the polymerization or cross-linkage of the stabilizing component of the liposome membrane. Polymerization occurs in response to exposure to ultraviolet light. The polymerization is accompanied by a change in color; therefore stabilization can be detected visually or spectrophotometrically by a color change in the liposomes.

The invention described herein has a number of advantages.

Firstly, by incorporation of the appropriate antigen into the liposomes, the binding of antibodies to the liposomes is restricted to those specific for diagnosis. Non-specific antibodies will not bind to the liposomes and, therefore, will not be detected.

Secondly, detection of antibodies is rapid and measured by simple colorimetric methods without the need for specialized equipment such as a fluorescence microscope.

Thirdly, both qualitative (visual) and quantitative (measured) aspects are possible in a single test, thereby allowing evaluation of antibody variation in a heterogeneous population of patients.

Fourthly, the test is exceedingly rapid; e.g., a response will be observed in a matter of minutes.

Lastly, the reagents used in the assay are non-toxic, non-radioactive, present no danger to the investigator, and do not require special handling.

4. DESCRIPTION OF THE INVENTION

The practice of one mode of the present invention involves the destabilization of the liposome membrane and the selective inhibition of destabilization. Accordingly, liposomes containing a destabilizing component, an entrapped indicator dye and an antigen incorporated into the bilayers are prepared so that upon destabilization of the liposome membrane the dye contacts the assay medium and changes color. Examples of destabilizing components of the liposome membranes include but are not limited to cardiolipin (in which case leakage is induced by the presence of divalent cations in the external medium) and phosphatidic acid in which case leakage is induced in the presence of normal serum, or influx is induced in the presence of divalent cations). At least two approaches are possible using this immunoassay:

(1) The antigen-modified liposomes described above are prepared so that they are destabilized when exposed to the assay medium yet stabilized by pre-incubation in the cognate antibody (i.e., destabilization is inhibited by the antibody-antigen interaction). Thus, according to this scheme, the presence of the antibody in the assay medium is indicated by no change in color whereas the absence of the antibody in the assay medium is indicated by a change in color.

(2) Conversely, the antigen-modified liposomes described above are prepared so that they are stabilized when exposed to the assay medium (i.e., the incorporated antigen inhibits destabilization) yet destabilized when exposed to a sample containing the cognate antibody. Thus, according to this second scheme, the presence of the antibody in the assay medium is indicated by a change in color whereas the absence of antibody in the assay medium is indicated by no change in color. In either approach, the degree of color change is an indication of the concentration of the antibody in solution.

The practice of another mode of the present invention involves the stabilization of the liposome membrane and the selective inhibition of stabilization. Accordingly, liposomes containing a stabilizing component and an antigen incorporated into the bilayers are prepared so that stabilization of the membrane occurs by polymerization of the stabilizing component when exposed to ultraviolet radiation. Polymerization and, therefore stabilization, is indicated by a change in color. The stabilizing components incorporated into these liposomes comprise diacetylenic phospholipids. (For the synthesis of these components, See Johnston, et al. 1980. Biochim. Biophys. Acta 602:57–69 and 213–216; and Leaver, et al. 1983. Biochim, Biophys. Acta 727:327–335). The synthesis can be accomplished chemically or by the biosynthetic incorporation of diacetylenic fatty acids into the biomembrane of the auxotroph, *Acholeplasma laidlawii*. These diacetylenic phospholipid molecules when irradiated with ultraviolet light in mono- and multilayers cross-link via the diacetylene groupings forming polymers, which, due to the conjugated nature of their backbone are highly colored (red). Liposomes prepared with these diacetylenic phospholipids can be polymerized by ultraviolet light to produce a red colored polymer. In fact the liposome bilayers may be composed entirely of diacetylenic phospholipids or mixtures of these with other lipid moieties. Furthermore, any mixture of diacetylenic phospholipids may be used to form liposomes because extensive cross-linking by exposure to ultraviolet light can occur despite the heterogeneity of the head group. The immunoassay of the present invention involves interference with this process. At least two approaches are possible:

(1) The capping model: The liposomes are prepared using diacetylenic phospholipids and antigen incorporated into the bilayers. If these antigen-modified liposomes are exposed to ultraviolet light, the presence of a sufficient amount of antigen will prevent extensive cross-linkage of the diacetylenic phospholipids and thus, there will be no change in color (without extensive cross-linkage the color will be yellow). However, if the liposomes are pre-incubated in the cognate antibody, under the proper conditions "capping" of the antigen can occur (i.e., the antigen will be segregated away from the diacetylenic phospholipids). Subsequent exposure of the capped liposomes to ultraviolet light will result in extensive cross-linkage of the diacetylenic phospholipids (because the diacetylenic phospholipids are now close enough to cross-link) and, therefore, in the appearance of a red color.

In a particularly useful modification of this mode of the invention, the diacetylenic phospholipid head group itself can be the antigen incorporated into a liposome bilayer comprising non-diacetylenic phospholipids. In this case, capping of the antigen by its cognate antibody results in aggregation of the diacetylenic phospholipids. Subsequent exposure to ultraviolet light will result in extensive cross-linking of the capped diacetylenic phospholipids and the appearance of a red color. Thus, the appearance of a red color in either embodiment of the capping model is indicative of the presence of the antibody.

(2) The non-capping model: The liposomes are prepared using diacetylenic phospholipids with a phosphatidic acid or any charged head group, and an antigen incorporated into the bilayers. If these liposomes are exposed to ions or to conditions that result in phase separation of the charged phosphatidic acid, then exposure to ultraviolet light will result in extensive cross-linkage of the diacetylenic phospholipids resulting in a red color. On the other hand, if the liposomes are pre-incubated in cognate antibody prior to exposure to the ion under conditions which do not lead to capping, phase separation of the phosphatidic acid will not occur. As a result, extensive cross-linkage will not occur after exposure to ultraviolet light because the antibody-antigen complexes will interfere with cross-linking of the diacetylenic phospholipids (the phospholipids will not be close enough for extensive cross-linkage). As a result, the red color will not develop.

In an alternate embodiment of the non-capping model, the diacetylenic phospholipid headgroup itself can be the antigen which is incorporated into a liposome bilayer comprising non-diacetylenic phospholipids. In this case the pre-incubation and binding of antibodies which do not cap the antigen will interfere with phase separation of the diacetylenic phospholipids when they are exposed to conditions which normally result in such phase separation. As a result, extensive cross-linking will not occur after exposure to ultraviolet light, and the red color will not develop. Therefore, in either embodiment of the non-capping model, the absence of a red color indicates the presence of antibody in the assay medium.

The immunoassays described herein may be used for a variety of purposes. For example, in a direct assay, the liposomes of the present invention may be mixed with serum samples to detect serum antibodies for diagnostic purposes. This embodiment is particularly useful for the diagnosis of various autoimmune diseases. Alternatively, the liposomes of the present invention may be used in conjunction with antibodies in competition assays in order to quantitatively detect antigen in test samples. For example, serial dilutions of a liposome preparation containing a known amount of antigen can be mixed with the cognate antibody in order to obtain a standard spectrophotometric curve for color change. When aliquots of a test solution containing an unknown amount of antigen are added to a parallel serial dilution of the liposome preparation, the change in the standard curve can be used to calculate the concentration of antigen in the test solution.

For the purposes of convenience, the description of the invention will be divided into two major areas: the liposomes, and diagnostic assays.

4.1. LIPOSOMES

The liposomes of the present invention can be prepared by a modification of a number of known methods (which are reviewed by Szoka and Papahadjopoulos.1980. Ann. Rev. Biophys. Bioeng. 9:467–508). The components used in the several embodiments of the present invention are described below.

4.1.1. THE ANTIGENS

In addition to the double tailed phospholipids (such as phosphatidylcholine) and the destabilizing component (such as cardiolipin or phosphatidic acid) or the stabilizing component (such as the diacetylenic phospholipids) there will be an antigen present in the liposome membrane. While lipid antigens are especially useful because they readily partition into the liposome membrane, any antigen which may be incorporated into the liposome membrane can be used; the choice of antigen merely depends upon the purpose of the immunoassay. For example, antigens which may be incorporated into the liposome membrane include but are not limited to: bacterial, rickettsial, viral, and chlamydial antigens. Such liposome preparations are useful in detecting serum immunoglobulins produced in response to infection of the host.

Other antigens which may be incorporated into the liposome membrane include but are not limited to: transplantation, tumor specific and carcinoembryonic antigens. Such liposome preparations are useful in detecting immunoglobulins produced in response to skin grafts, organ transplants, tumors or malignant cells present in the host.

Still other antigens which may be incorporated into the liposome membrane include but are not limited to: smooth muscle antigen, acetylcholine, pancreatic antigens, mitochondrial antigens, skin and sperm antigens, and nucleic acids as antigens. These liposomes are particularly useful for detecting antibodies that are produced in autoimmune disorders (e.g., including but not limited to the disorders listed in Table I).

Finally, immunoglobulins themselves may be incorporated into the liposome bilayers. These liposomes may be used for the detection of antiidiotypic antibodies or for the detection of their corresponding antigen. Thus, antibodies directed against drugs or hormones, etc., may be incorporated into the liposome bilayers. For example anti-chorionic gonadotropic hormone may be incorporated into liposome bilayers. These liposomes may be used to detect the hormone in blood or urine samples of female patients as an indication of pregnancy; alternatively, the detection of this hormone in male patients may indicate a testicular cancer.

While lipid antigens can be incorporated into the liposome membranes simply by adding the lipid antigen to the liposome ingredients, non-lipid antigens may have to be modified in order to ensure their incorporation into the bilayer. The non-lipid antigens may be incorporated into the liposome membrane by covalently attaching the antigen to a lipid moiety of the liposome. Two methods for the formation of such lipid-antigen conjugates which can be incorporated into the liposome bilayers are described in U.S. patent application entitled "Improved Method of Conjugate Formation Using N-Hydroxysuccinimide" by Lenk et al., filed Sept. 19, 1983, and in U.S. patent application entitled "Localized Delivery of Fibronectin Conjugates", by Weiner et al., filed Sept. 19, 1983, which are both incorporated by reference herein.

4.1.2. LIPOSOMES INCORPORATING A DESTABILIZING COMPONENT

Liposomes of the invention can be formed from certain amphipathic lipids. In contrast to lipid aggregates such as micelles and surface monolayers, liposomes involve self-sealing bilayers which form closed vesicles. Such bilayers can be produced from a number of flexible double tailed phospholipids, such as phosphatidylcholines of the formula

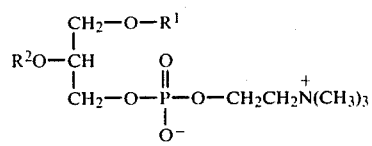

in which each of $R^1$ and $R^2$ is the acyl residue of the same or different fatty acid. $R^1$ and $R^2$ will generally have from 14 to 20 carbon atoms and may be saturated or unsaturated, e.g., tetradecanoyl, tetradec-9-enoyl, hexadecanoyl, hexadec-9-anoyl, octadecanoyl and octadec-9-enoyl. As noted, the $R^1$ and $R^2$ can be and often are different. Moreover, when unsaturation is present, the chain generally, but not necessarily, will define the cis configuration and will be present in the $R^2$ group. Most desirable $R^1$ and $R^2$ groups will be chosen to provide one double bond per phospholipid molecule. Particularly preferred are $R^1$ being palmitoyl (hexadecanoyl) and $R^2$ being oleoyl (cis-octadec-9-enoyl).

In addition to the double-tailed phospholipids there will be present a lipid which serves as a destabilizing component. The preferred destabilizing component can be either a cardiolipin (diphosphatidylglycerol) or a phosphatidic acid. Liposome membranes composed of a phospholipid and a cardiolipin are unstable in the presence of divalent cations such as magnesium. This is probably due to the conversion of the membrane from a lamellar to a hexagonal configuration which destabilizes the membrane and allows the liposomal contents to leak out. Liposome membranes composed of a phospholipid and a phosphatidic acid are also unstable in the presence of divalent cations such as magnesium (in fact, these liposomes are unstable in normal serum). This is probably due to a phase separation of the phosphatidic acid resulting in the formation of an ionophore which allows the influx of ions from the external assay medium into the aqueous space of the liposome.

When antigens are incorporated into a liposome membrane containing a destabilizing component (e.g., a cardiolipin or a phosphatidic acid), the antigen itself may stabilize the membrane so that no leakage or influx occurs in the presence of cations. However, when this liposome preparation is incubated with a cognate antibody, a phase separation may occur such that the destabilizing component sites on the liposome membrane are freed; subsequent, exposure to a cation such as magnesium results in destabilization of the liposome membrane. Thus the presence of antibody in the serum is indicated by destabilization of the membrane.

The cationic dependent destabilization of the liposome membrane in liposome preparations containing a destabilizing component (e.g., cardiolipin or phosphatidic acid) can be prevented by the exposure to antibodies which bind to the destabilizing component itself. Although the reasons for such stabilization are unclear, it is possible that antibodies which bind to the cardiolipin or the phosphatidic acid prevent the conversion to a hexagon configuration or to an ionophore, respectively, and stabilize the liposomes when exposed to cations.

In a particularly useful embodiment of the invention, a destabilizing component which also serves as an antigen can be incorporated into the liposome membrane.

In fact, certain lipids which serve as antigens for antibodies specifically found in patients with SLE can be incorporated into liposome membranes as destabilizing components. Several such lipids are known but from the standpoint of availability, economics and performance, a phosphatidic acid or a cardiolipin (diphosphatidylglycerol) are preferred. The molar ratio of phosphatidylcholine to such lipid antigen will be from about 1:7 to about 7:1. One particularly satisfactory ratio is about 3:4 of phosphatidylcholine:lipid antigen. The advantage of this embodiment is that the stabilizing/destabilizing component itself serves as the antigen. When these liposomes are incubated with SLE serum, the antibodies in the serum bind to the cardiolipin or the phosphatidic acid present in the liposome membrane and prevent destabilization in the presence of cations. Thus, the presence of antibody in the sera is indicated by stabilization of the membrane.

It will be appreciated that multicomponent liposomes such as herein described involve a high degree of component interaction and interdependency. Hence the interaction through van der Waal's attractive forces and steric repulsive forces of the various hydrophobic "tail" groups ($R^1$ and $R^2$) generally determine the nature of the bilayer's interior whereas steric effects, dipolar forces and electrostatic forces involving the hydrophilic "head" groups generally determine the nature of the bilayer's interfacial region. The nature of either group can also affect the nature of the other. The dynamic packing properties of the lipids which comprise a multicomponent liposome are determined by the complex interrelation of the component molecules.

It is desirable in some instances to incorporate a small amount of a rigid molecule such as a steroid (cholesterol or hydrocortisone) to modify the stability of the liposome. The presence of such rigid molecules in the liposome appears to alter the order of the hydrophobic tails of the phospholipid. Generally, this amount of steroid will be from about 5 to about 30 molar percent, based on the total amount of phosphatidylcholine and antigen which is present. The influence of such stability altering components on the liposome involves a number of physicochemical characteristics which are easily determined but which are not characteristic of any given class of chemical compounds. Hence while cholesterol and dihydrocortisone will increase stability and reduce permeability of some liposome bilayers, they will decrease stability and increase permeability in others. Various thermodynamic and geometric theories explaining different properties of bilayer components have been proposed [see e.g., Israelachvili et al., Quat. Rev. Biophysics, 23 (2):121–200 (1980)], but in any event, the stabilizing effect of any given substance can be determined readily on an empirical basis utilizing spectrophotometric methods [see Weissmann et al., Proc. Nat. Acad. Sci. USA, 73, (2):510 (1976)].

In addition to the above components, the inclusion of a small amount, from about 10 to about 20 molar percent, of a liposome compatible negatively charged compound, e.g., a difatty acid phosphatidyl- glycerol or difatty acid alcohol phosphate ester, will be desirable. The function of this component, as for example dipalmitoylphosphatidylglycerol (DPPG) or dicetylphosphate, is to increase the net negative surface charge of the bilayer. The addition of DPPG also confers stability. It has also been found desirable to include a small amount, e.g., from 1 to 5 molar percent, of an antioxidant which is lipid-compatible, e.g., alpha-tocopherol.

For the SLE immunoassay, it is preferred to use potassium or cesium salt forms ot the anionic lipids, i.e., cardiolipin and dipalmitoylphosphatidylglycerol, since these forms substantially reduce false positive reactions in the final assay and increase solubility in solvent during the formation step. For example, liposomes formulated from the sodium, ammonium or lithium salts of anionic lipids while producing sporadic results for SLE, in some instances also produce false positives in the presence of rheumatoid factor. Thus, the sodium, ammonium and lithium salt forms should be avoided. The salt form is prepared by reacting a hydroxide of the metal selected with the free acid form of an anionic lipid. The free acid form of the anionic lipid is prepared by mixing a lipid with a solvent such as chloroform and adding polyanionicion exchange beads. The suspension is then centrifuged and the supernatant containing the free acid of the lipid is removed. The free acid of the lipid is neutralized to pH 7 by the addition of the metal hydroxide to form the salt. Most preferably the cardiolipin is associated with cesium cation and dipalmitoylphosphatidylglycerol with the potassium cation.

A preferred bilayer composition for the SLE immunoassay includes phosphatidylcholine, cardiolipin, cholesterol, alpha-tocopherol and a phosphatidylglycerol in a molar ratio of about 3:4:1.9:0.1:1.

These liposome bilayers, also have entrapped therein a metallochromic (colorimetric) indicator which is sensitive to divalent cations. For example, arsenazo III [2,7-bis-(2-arsenophenylazo)-1,8-dihydroxynaphthalene-3,6-disulfonic acid] is normally red but turns blue in the presence of divalent metal cations, such as magnesium.

Thus, destabilization of the liposome membrane (i.e., release of entrapped material or influx of ions from the surrounding medium) in the presence of cations results in a change of color of the indicator dye.

The preferred method of preparing liposomes involves injecting an ethereal solution of the bilayer components into a large volume of aqueous buffer solution containing the dye. Alternatively, lipids are prepared and dried, as by rotary evaporation from a suitable nonaqueous liquid such as chloroform, and combined with a solution of the indicator in buffer solution [0.145M NaCl-KCl, about 5 mM 4-2(2-hydroxyethyl)-piperazine-2-ethane-sulfonic acid] to effect swelling and concomitant entrapment.

In either case the liposome mixture is chromatographed to separate excess, nonentrapped indicator from liposome-entrapped indicator, elution being readily monitored visually or by spectroscopy. Often it is advantageous or sometimes necessary to hold the liposome mixture under vacuum for a period of time, as for example, one or two hours, prior to chromatography in order to remove substantially all of the remaining solvent.

4.1.3. LIPOSOMES INCORPORATING A STABILIZING COMPONENT

The diacetylenic phospholipids incorporated into liposomes for use in the capping model may be any of a number of phospholipids. As explained previously, antigen can be incorporated into the liposome membrane in an amount sufficient to inhibit cross-linking upon exposure to ultraviolet light. However, capping of the antigen by its cognate antibody segregates the antigen away from the diacetylenic phospholipids, and thus allows areas of extensive cross-linking to occur after exposure to ultraviolet light resulting in the formaton of a red polymer. Accordingly any mixture of the diacetylenic phospholipids may be used because, despite heterogeneity of the lipid headgroups, extensive polymerization by ultraviolet light can occur in the liposome. Therefore multicomponent liposomes can be made from diacetylenic phospholipids or mixtures of these with conventional phospholipids.

In the alternative embodiment of the capping model, the diacetylenic phospholipid is the antigen itself. Accordingly, the diacetylenic phospholipid antigen is incorporated into a bilayer comprising non-diacetylenic phospholipids. Subsequent antibody-mediated capping of the diacetylenic phospholipids results in aggregation which form areas of extensive cross-linking upon exposure to ultraviolet light which is indicated by the formation of a red color. In this embodiment of the capping model, where the diacetylenic phospholipid head group is the antigen, homogeneity of the antigenic head groups is necessary so that the antibody-mediated capping will occur. Thus, when preparing liposomes for use in this particular embodiment, the diacetylenic phospholipids containing a homogeneous head group are incorporated into a bilayer that may be composed of any assortment of non-diacetylenic phosolipids.

The liposomes used in the non-capping model comprise a bilayer containing diacetylenic phospholipids with a charged head group such as a phosphatidic acid head group and an antigen which is incorporated into the diacetylenic phospholipid bilayer. Phase separation in the presence of a divalent cation is prevented by exposure of the liposomes to cognate antibody, probably because the antibody-antigen complexes change the supramolecular structure of the liposome. Any combination of diacetylenic phospholipids may be used. However, the embodiment in which the diacetylenic phospholipid is the antigen itself, the antigenic head group of the diacetylenic phospholipids should be homogeneous in order to allow antibody-antigen formation and prevention of phase separation. The other components of the lipid membrane, however, can be any variety of non-diacetylenic phospholipids.

Similar to the liposomes containing a destabilizing component, the liposomes containing a stabilizing component may contain a number of other membrane constituents. Thus, it may be desirable to incorporate a small amount of a rigid molecule such as a steroid (e.g., cholesterol or hydrocortisone) to modify the stability of the liposomes.

4.2. DIAGNOSTIC ASSAYS

Three major embodiments (I, II, and III) for diagnostic assays are described below. The three embodiments are based on the discovery that the increase in the permeability of the liposome bilayer which is observed in certain environments will be impeded or blocked by antibodies present in the surrounding medium. The antibodies are said to stabilize the liposome. "Stabilization" as used in the embodiment of the present invention refers to the preservation of the supramolecular structure or membrane architecture of the liposome. The precise mechanism by which this stabilization occurs is not fully understood. It is known that certain liposomes increase their permeability in the presence of divalent cations such as magnesium. Other liposomes are destabilized simply in the presence of normal serum. This destabilization will result in lysis of the liposome bilayer with release or "leakage" of any material which is entrapped therein. In some cases "leakage" refers to the movement (influx) of ions from the external environment into the aqueous spaces of the liposome. Surprisingly, however, this destabilization can be selectively blocked, i.e., the liposome structure is stabilized, by antibodies. Consequently, by entrapping a metallochromic indicator within the liposome bilayer, the presence of certain antibodies can be detected by observing the degree of blockage of the destabilization which is reflected by absence of a color change in the indicator.

For the purposes of clarity, the following subsections describe three preferred embodiments of the invention as it applies to the detection of SLE antibodies. This is not meant to limit the scope of the invention, however, as any antigen can be incorporated into a liposome membrane which entraps a colorimetric indicator for the detection of its corresponding antibody in the test solution according to the practice of this invention.

4.2.1. EMBODIMENT I

In a first embodiment (I) of the present invention, a liposome composition is prepared which is susceptible to serum (normal)-induced leakage. For this purpose, it is preferable to utilize a phosphatidic acid as the lipid antigen for SLE in the liposomes, e.g., a liposome comprising a flexible double tailed phosphatidylcholine and a phosphatidic acid in a molar ratio of from about 1:7 to about 7:1, respectively, preferably from about 2:5 to about 4:3. A particularly desirable liposome comprises 3 molar parts of a phosphatidylcholine and 4 molar parts of phosphatidic acid (optionally together with the other components described above) with the indicator entrapped therein (as hereinafter described). Futhermore, 1-palimitoyl-2-oleoyl-phosphatidic acid is the preferred lipid antigen. Such liposomes will be stable in buffer but will demonstrate leakage in normal serum, thereby releasing the indicator. However, if such liposomes are first brought into contact with SLE serum, the leakage which would otherwise be observed is diminished or precluded. Consequently, challenge with a divalent metal cation to which the indicator is responsive, most notably magnesium, will produce a color change in the case of normal serum (and in fact serum from numerous diseased conditions) due to serum-induced leakage of the indicator. No color change (or one which develops at a far slower rate) will be observed in the case of a liposome which first is brought in contact with SLE serum.

4.2.2. EMBODIMENT II

In a second embodiment (II) of the invention, a liposome composition is prepared similar to that described in Embodiment I but utilizing, cardiolipin in place of the phosphatidic acid. Such a composition will not develop leakage in the presence of serum (or for that matter in the presence of buffer). Leakage however can be induced by the addition of divalent ions such as magnesium. Again, such leakage is inhibited or reduced if the liposome is first brought in contact with SLE antibodies.

In this embodiment, therefore, the addition of magnesium ions not only induces leakage in the liposome composition, it also causes a color change in indicator which has "leaked" out of the liposome. In contrast, the same liposome composition which has come in contact with SLE serum will show no leakage (or leakage at a greatly reduced rate) in the presence of magnesium ions. Consequently little or no color change will occur.

The concentration of magnesium ion needed according to this embodiment is relatively small; generally a 5 to 80 millimolar solution is adequate. Excessively high concentrations should be avoided as these can produce leakage even in SLE serum treated liposomes. There also is an interplay between the liposome concentration and the amount of magnesium ion added and thus it is convenient to define a minimum lysis concentration (MLC) for each liposome composition; i.e., that concentration of magnesium ion which is just sufficient to effect release of the indicator from the liposome bilayer in the presence of normal serum. This concentration can be easily determined by titration with increasing concentrations of magnesium ion.

4.2.3. EMBODIMENT III

In a third embodiment (III) of the invention, liposomes containing a phosphatidic acid and a colorimetric indicator are used. When these liposomes are treated with $Ca^{++}$, a phase separation or clustering of the phosphatidic acid occurs resulting in the transport of $Ca^{++}$ to the interior of the liposome where it produces a color change in the indicator. When the antigen containing liposome is brought in contact with SLE antibodies, however, the antibodies bind to the antigen, inhibiting this clustering and thus stabilizing the membrane architecture of the liposome. $Ca^{++}$ will be transferred into the interior of the liposome at a very slow rate and no color change will be detected. (However, over time, there will be a gradual change in color.) Thus, as with the other embodiments, addition of SLE serum to the liposome, results in a little or no color change in the indicator.

The preferred liposome composition for this embodiment comprises a flexible double tailed phosphatidylcholine and a phosphatidic acid in molar ratios of from about 9:1 to about 3:7, respectively. The preferable phosphatidic acid is dipalmitoylphosphatidic acid and the preferable liposomes comprise egg phosphatidylcholine, dipalmitoylphosphatidic acid, cholesterol and dicetylphosphate in molar ratios of about 7:1:1:1, respectively.

While there are no critical operating conditions for the assay, they should be non-inhibiting and non-destructive. Aqueous media (other than magnesium solution) should be free of divalent metals such as calcium ion and preferably prepared from deionized water. Detergents and other chaotropic materials should be absent as should any impurities with which the antibodies may react.

5. EXAMPLE IMMUNOASSAYS FOR SLE

The following examples will serve to further typify the nature of the invention without being a limitation on the scope thereof.

5.1. EXAMPLE 1 PREPARATION OF LIPOSOMES

Liposomes are prepared according to a modification of the method of Deamer and Bangham (Biochim. Biophys. Acta, 443: 629–634 [1976]). All materials and equipment should be free of divalent metal cations. 1-Palimitoyl-2-oleoyl-phosphatidylcholine, cardiolipin, cholesterol, alpha-tocopherol and dipalmitoylphosphatidylglycerol in a 3:4:1.9:0.1:1 molar ratio are solubilized in petroleum ether. Ten milliliters of ether solution (40 micromoles of lipid) are placed in a 20 ml glass syringe with a Teflon plunger which is attached to a vertical infusion pump.

A suspension of 4.5 mM arsenazo III (hereinafter A III) in 2 ml of 5 mM Hepes buffer (N-2-hydroxyethylpiperazine-N'-2-ethanesulfonic acid) at pH 7.2, containing 0.145M NaCl/KCl is placed in Leibig condenser into which a rubber stopper (bottom opening) has previously been placed. The condenser is heated to 54° C. with a circulating water bath and nitrogen is bubbled through the aqueous phase. A 22 gauge needle is inserted through the rubber stopper at the bottom of the condenser.

The petroleum ether phase is then injected into the aqueous phase at a rate of 0.5 ml/min. As the ether evaporates and escapes, the liposome suspension remains. This suspension is passed through a column of Sepharose 4B, eluting with buffer, to remove excess and unsequestered A III, the liposome-entrapped A III (red) being eluted from the column in the void volume. Optionally the suspension to be chromatographed can be held under vacuum (water aspirator) for from about one to five hours to remove excess petroleum ether prior to passage through the column. This material is then diluted with Hepes buffer to a concentration at which one can best distinguish between lupus positive sera and normal sera. This is typically an optical density of approximately 0.12 at 750 nanometers.

5.2 EXAMPLE 2 PREPARATION OF ANIONIC LIPIDS FOR EMBODIMENT II

Three grams of 100–200 mesh beads of sulfonated polystyrene (Biorad AG50W-X8) are washed once with 1:1 methanol:water and three times with 1:1 methanol:chloroform. Twenty-five mg of cardiolipin (commercially obtained, sodium salt) are added and allowed to remain in contact with the beads for 2 minutes. The cardiolipin (free acid) is separated from the suspension by centrifugation and titrated with 0.M cesium hydroxide in methanol to pH 7. Recovery is determined by a Bartlett assay for inorganic phosphate (Kates, "Technology of Lipidology", North-Holland American Elsevier, 1975). The product should produce a single spot on TLC (65:25:4 chloroform:methanol:water).

Following the same procedure with dipalmitoylphosphatidylglycerol (sodium salt) but titrating with 0.M methanolic potassium hydroxide, there is obtained the potassium salt form.

These materials, namely cardiolipin (cesium salt) and dipalmitoylphosphatidylglycerol when utilized in the procedure of Example 1 produce a liposome composition of increased selectivity to SLE antibodies.

5.3. EXAMPLE 3 EMBODIMENT I

As an example of Embodiment I, liposomes are prepared according to the procedure of Example 1 utilizing, however, phosphatidic acid in place of cardiolipin. When utilized in the actual assay, leakage will occur upon addition of the serum. The leakage will be detected upon addition of magnesium ion.

5.4. EXAMPLE 4 EMBODIMENT II

As an example of Embodiment II, aliquots of the liposomes (red) are placed in two glass tubes. To one tube is added an SLE test serum and to the other normal serum (control). Based upon the volume in each tube, a serum dilution equal to 1:16 may be prepared. (In practice, several different dilutions, and therefore several tubes, could be used). The same dilution is made for both the SLE test serum and normal serum. After serum addition, the liposomes are incubated for 1 to 5 minutes at about 25° C. Following the incubation, magnesium chloride solution (e.g., 50 mM final concentration) is added to each of the tubes. The normal serum control will turn blue within 5 minutes while the lupus serum test sample will remain red for at least 3 hours longer than the normal serum.

Alternatively, the test sample and normal serum control are serially diluted. If at any dilution there is a substantial delay in the color change induced by the test sample as compared to the serum control, the test is considered positive.

5.5. EXAMPLE 5 EMBODIMENT III

As an example of Embodiment III, one hundred microliters of liposomes (red) are placed in three glass tubes and diluted with Hepes buffer up to 0.2 ml. One tube constitutes a buffer blank, the second is an SLE test serum and the third serves as a normal serum control. Based upon the 0.3 ml volume in each tube, a serum dilution equal to 1:16 is calculated. (In practice, several different dilutions, and therefore several tubes, could be used). The same dilution is made for both the SLE test serum and normal serum. After serum addition, the liposomes are incubated for 5 minutes at about 25° C. Following the incubation, 80 mM calcium chloride (final concentration) is added to each of the tubes. The buffer control will turn blue within 10 minutes. The normal serum control will turn blue before 30 minutes, and the lupus serum test will remain red for at least 30 minutes longer than the normal serum. Alternatively, the test sample and normal serum control are serially diluted. If at any dilution there is a substantial delay in the color change induced by the test sample as compared to the serum control, the test is considered positive.

5.6. EXAMPLE 6 BLIND STUDIES

A blind study (involving Embodiment II) included serum samples from the following sources: known lupus patients, patients exhibiting clinical symptoms of lupus but a negative clathridia test, patients showing antinuclear antibodies but no clinical symptoms, patients with scleroderma, patients with a positive VDR test (syphilis), patients with Sjogren's Syndrome and normal patients. The assay gave a proper response in 19 out of 20 unknowns. The only false negative was a patient suffering from both syphilis and lupus. Significantly, and in contrast to other tests, a patient with syphilis but not lupus did not produce a false positive.

In a second blind study of 80 samples of sera (also involving Embodiment II) which included previously diagnosed rheumatoid arthritis, scleroderma, Sjogren's Syndrome, mixed connective tissue disease, and controls, the following results were obtained:

|                     | No. Tested | Positive | Negative |
| ------------------- | ---------- | -------- | -------- |
| SLE                 | 19         | 17       | 2        |
| Rheumatoid Arthritis| 19         | 4        | 15       |
| Scleroderma         | 14         | 0        | 14       |
| Sjogren's Syndrome  | 2          | 0        | 2        |
| MCTD                | 2          | 2        | 0        |
| Controls            | 24         | 1        | 23       |

While the invention has been described with reference to its preferred embodiments thereof, it will be appreciated by those of ordinary skill in the art that various changes can be made in the process and compositions without departing from the basic spirit and scope of the invention.

What is claimed is:

1. A method for detecting antibodies in serum, comprising:
   (a) contacting serum, for a period of time at least sufficient to permit equilibration of binding between an antigen and its cognate antibody, with liposomes having a multicomponent bilayer comprising a flexible double tailed phospholipid and a destabilization component, wherein at least one of the liposome membrane constituents is an antigen;
   (b) exposing the liposomes to conditions which cause destabilization of the liposomes in the absence of cognate antibodies directed against the antigen and which do not cause destabilization of the liposomes in the presence of the cognate antibodies;
   (c) detecting any destabilization of the liposome, the method being performed under conditions noninhibiting to the binding between the antigen and its cognate antibody.

2. The method according to claim 1 wherein the destabilizing agent is a cardiolipin.

3. The method according to claim 1 wherein the destabilizing agent is a phosphatidic acid.

4. A method for detecting antibodies in serum, comprising:
   (a) contacting serum, for a period of time at least sufficient to permit equilibration of binding between an antigen and its cognate antibody, with liposomes having a multicomponent bilayer comprising a flexible double tailed phospholipid and a destabilization component, wherein at least one of the liposome membrane constituents is an antigen;
   (b) exposing the liposomes to conditions which do not cause destabilization of the liposomes in the absence of cognate antibodies directed against the antigen and which cause destabilization of the liposomes in the presence of the cognate antibodies;
   (c) detecting any destabilization of the liposome, the method being performed under conditions noninhibiting to the binding between the antigen and its cognate antibody.

5. The method according to claim 4 wherein the destabilizing agent is a cardiolipin.

6. The method according to claim 4 wherein the destabilizing agent is a phosphatidic acid.

7. The method according to claim 2 for detecting SLE antibodies in serum wherein the phospholipid phosphatidylcholine and the antigen is cardiolipin in a molar ratio of from about 1:7 to about 7:1 respectively.

8. The method according to claim 7, wherein said ratio is from about 2:5 to about 4:3.

9. The method according to claim 7, wherein said liposomes contain entrapped therein a divalent cation responsive colorimetric indicator, and said conditions causing destabilization comprise contacting said liposomes with divalent cations which results in leakage and a change in color of the indicator.

10. The method according to claim 9, wherein the divalent cations are magnesium or calcium cations.

11. The method according to claim 3 for detecting SLE antibodies in serum wherein the phospholipid is phosphatidylcholine and the antigen is phosphatidic acid in molar ratios of from about 9:1 to about 3:7, respectively, said liposomes being unstable in the presence of calcium ions unless SLE antibodies are present and wherein the condition which cause destabilization of the liposomes comprise exposing said liposomes to calcium ions.

12. The method according to claim 11, wherein said phosphatidic acid is dipalmitoylphosphatidic acid, and said liposomes have a multicomponent liposome bilayer comprising egg phosphatidylcholine, dipalmitoylphosphatidic acid, cholesterol and dicetylphosphate in molar ratios of about 7:1:1:1, respectively.

13. The method according to claim 11, wherein said liposomes contain entrapped therein a divalent cation responsive colorimetric indicator, and said destablization results in an influx of divalent cations into the liposomes which results in a change in color of the indicator.

14. A method according to claim 3 for detecting SLE antibodies in serum wherein the phospholipid is phosphatidylcholine and the antigen is phosphatidic acid in a molar ratio of from about 1:7 to about 7:1, respectively, said liposomes being stable in the presence of serum containing SLE antibodies and unstable in the presence of serum not containing SLE antibodies.

15. The method according to claim 14, wherein said ratio is from about 2:5 to about 4:3.

16. The method according to claim 14, wherein said phosphatidic acid is 1-palmitoyl-2-oleoylphosphatidic acid.

17. The method according to claim 14, wherein said liposomes contain entrapped therein a colorimetric indicator, and said instability is detected by a color change in said indicator which is released from the liposomes in the absence of SLE antibodies.

18. The method according to claim 17, wherein said indicator is responsive to divalent metal ions and is exposed to divalent cations upon release from the liposomes.

19. The method according to claim 18, wherein the divalent metal ions are magnesium ions.

20. The method according to claim 7, 11 or 14, wherein anionic lipid components of the multicomponent bilayer are cesium or potassium salts.

21. The method according to claim 7, 11 or 14, wherein said phosphatidylcholine is 1-palmitoyl-2-oleoyl-phosphatidylcholine.

22. The method according to claim 7, 11 or 14, wherein said liposome bilayer contains a stabilizing amount of a rigid steroid stabilizer.

23. The method according to claim 22, wherein said steroid is cholesterol.

24. The method according to claim 23, wherein the stabilizing amount is from about 5 to about 30 molar percent, relative to the total amount of said phosphatidylcholine and phosphatidic acid or cardiolipin.

25. The method according to claim 7 or 14, wherein said liposome bilayer contains from about 10 to about 20 molar percent, relative to the total amount of said phosphatidylcholine and phosphatidic acid or cardiolipin, of a liposome compatible negatively charged compound.

26. The method according to claim 25, wherein said liposome compatible negatively charged compound is phosphatidylglycerol.

27. The method according to claim 26, wherein said phosphatidylglycerol is dipalmitoyl-phosphatidylglycerol.

28. The method according to claim 11, wherein said liposome bilayer contains from about 10 to about 20 molar percent, relative to the total amount of phosphatidylcholine and phosphatidic acid, of dicetylphosphate.

29. The method according to claim 7, 11 or 14, wherein said liposome bilayer contains a stabilizing amount of an antioxidant.

30. The method according to claim 29, wherein said antioxidant is alpha-tocopherol in an amount corresponding to from about 1 to about 5 molar percent of the total amount of said phosphatidylcholine and phosphatidic acid or cardiolipin.

31. The method according to claim 7, wherein said bilayer comprises 1-palmitoyl-2-oleoyl-phosphatidylcholine, cardiolipin, cholesterol, alpha-tocopherol and dipalmitoyl phosphatidylglycerol in a molar ratio of about 3:4:1.9:0.1:1, respectively.

32. The method according to claim 14, wherein said bilayer comprises 1-palmitoyl-2-oleoyl-phosphatidylcholine, 1-palmitoyl-2-oleoyl-phosphatidic acid, cholesterol, alpha-tocopherol and dipalmitoyl phosphatidylglycerol in a molar ratio of about 3:4:1.9:0.1:1, respectively.

33. The method according to claim 9, 13 or 17, wherein said indicator is arsenazo III.

34. A liposome composition comprising liposome vesicles, said vesicles having (i) a multicomponent liposome bilayer comprising a flexible double tailed phosphatidylcholine and a lipid antigen for SLE antibodies in a molar ratio of from about 1:7 to about 9:1, respectively, and (ii) a colorimetric indicator entrapped within said liposome.

35. A composition according to claim 34, wherein said indicator is a divalent cation responsive colorimetric indicator.

36. A composition according to claim 34, wherein said ratio is from about 2:5 to about 4:3.

37. A composition according to claim 34, wherein said lipid antigen is a phosphatidic acid or cardiolipin.

38. A composition according to claim 34, wherein said phosphatidylcholine is 1-palimitoyl-2-oleoyl-phosphatidylcholine.

39. A composition of claim 34, wherein said vesicles have a multicomponent liposome bilayer comprising egg phosphatidylcholine, dipalmitoylphosphatidic acid, cholesterol and dicetylphosphate in molar ratios of about 1:1:1, respectively.

40. A composition according to claim 34, wherein said liposome bilayer contains a stabilizing amount of a rigid steroid stabilizer.

41. A composition according to claim 40, wherein said steroid is cholesterol.

42. A composition according to claim 40, wherein the stabilizing amount is from about 5 to about 30 molar percent, relative to the total of amount of said phosphatidylcholine and said lipid antigen.

43. A composition according to claim 34, wherein said liposome bilayer contains from about 10 to about 20 molar percent, relative to the total of said phosphatidylcholine and said lipid antigen, of a liposome compatible negatively charged compound.

44. A composition according to claim 43, wherein said liposome compatible negatively charged compound is a phosphatidylglycerol.

45. A composition according to claim 44, wherein said phosphatidylglycerol is dipalmitoyl-phosphatidylglycerol.

46. A composition according to claim 34, wherein said liposome bilayer contains a stabilizing amount of an antioxidant.

47. A composition according to claim 46, wherein said antioxidant is alpha-tocopherol in an amount corresponding to from about 1 to about 5 molar percent of the total amount of said phosphatidylcholine and said lipid antigen.

48. A composition according to claim 34, wherein said liposome bilayer comprises 1-palmitoyl-2-oleoyl-phosphatidylcholine, cardiolipin, cholesterol, alpha-tocopherol and dipalmitoyl phosphatidylglycerol in a molar ratio of about 3:4:1.9:0.1:1, respectively.

49. A composition according to claim 34, wherein said liposome bilayer comprises 1-palmitoyl-2-oleoyl-phosphatidylcholine, 1-palmitoyl-2-oleoyl-phosphatidic acid, cholesterol, alpha-tocopherol and dipalmitoyl-phosphatidylglycerol in a molar ratio of about 3:4:1.9:0.1:1, respectively.

50. A composition according to claim 34 or 48, wherein said indicator is arsenazo III.

51. A composition according to claim 34, wherein said lipid antigen is a cesium or potassium salt.

52. A composition according to claim 34, wherein said lipid antigen is the cesium salt of cardiolipin and wherein said liposome bilayer further comprises the potassium salt of dipalmitoylphosphatidylglycerol.

53. A method for preparing liposomes having a compound entrapped therein, comprising:
  (a) forming a dispersion of at least one amphipathic lipid in an organic solvent;
  (b) forming an aqueous mixture containing a compound to be entrapped in the liposomes;
  (c) injecting the dispersion into the aqueous mixture heated to a temperature above the boiling point of the organic solvent to form, as the organic solvent escapes, a suspension of liposomes having said compounds entrapped therein; and
  (d) exposing the suspension to a vacuum produced by a water aspirator for from about one to five hours to remove excess remaining organic solvent.

54. A method for detecting antibodies in serum, comprising:
  (a) contacting serum, for a period of time at least sufficient to permit equilibration of binding between an antigen and its cognate antibody, with liposomes having a multicomponent bilayer comprising a diacetylenic phospholipid and an antigen;
  (b) exposing the liposomes to ultraviolet light; and
  (b) detecting any polymerization of the liposome membrane,
the method being performed under conditions non-inhibiting to the binding between the antigen and its cognate antibody.

55. The method according to claim 54 wherein the antigen is a diacetylenic phospholipid and the other bilayer components are non-diacetylenic phospholipids.

56. The method according to claim 54 wherein the diacetylenic phospholipid has a charged polar head group and further comprising the step prior to exposure to ultraviolet light, of exposing the liposomes to conditions which cause phase separation of the polar head group in the absence of cognate antibodies directed against the antigen and which do not cause phase separation of the phosphatidic acid in the presence of the cognate antibodies.

57. The method according to claim 56 wherein the antigen is a diacetylenic phospholipid and the other bilayer components are non-diacetylenic phospholipids.

* * * * *